(12) United States Patent
Ma et al.

(10) Patent No.: US 11,304,684 B2
(45) Date of Patent: Apr. 19, 2022

(54) DEVICE FOR COLLECTING BREATH AND AIDING MEASUREMENT OF TRACE COMPONENT IN BREATH AND USAGE METHOD THEREOF

(71) Applicant: Shenzhen Seekya Bio-Sci & Tech Co., Ltd., Guangdong (CN)

(72) Inventors: Yongjian Ma, Guangdong (CN); Yongqiang Ji, Guangdong (CN); Guoliang Zhu, Guangdong (CN)

(73) Assignee: Shenzhen Seekya Bio-Sci & Tech Co., Ltd., Shenzhen (CN)

( * ) Notice: Subject to any disclaimer, the term of this patent is extended or adjusted under 35 U.S.C. 154(b) by 471 days.

(21) Appl. No.: 16/326,366

(22) PCT Filed: Aug. 18, 2016

(86) PCT No.: PCT/CN2016/095878
§ 371 (c)(1),
(2) Date: Feb. 18, 2019

(87) PCT Pub. No.: WO2018/032465
PCT Pub. Date: Feb. 22, 2018

(65) Prior Publication Data
US 2020/0229799 A1 Jul. 23, 2020

(51) Int. Cl.
*A61B 5/08* (2006.01)
*A61B 10/00* (2006.01)
(Continued)

(52) U.S. Cl.
CPC .............. *A61B 10/00* (2013.01); *A61B 5/097* (2013.01); *G01N 1/22* (2013.01); *A61B 2010/0087* (2013.01); *G01N 2001/2244* (2013.01)

(58) Field of Classification Search
CPC . A61B 10/00; A61B 5/097; A61B 2010/0087; A61B 5/4845; A61B 5/082; G01N 1/22; G01N 2001/2244
See application file for complete search history.

(56) References Cited

U.S. PATENT DOCUMENTS

| 4,947,861 A * | 8/1990 | Hamilton ........... G01N 33/0054 |
| | | 600/532 |
| 2003/0024331 A1* | 2/2003 | Hamilton .............. F16K 15/147 |
| | | 73/864.63 |

(Continued)

FOREIGN PATENT DOCUMENTS

WO    WO-0201182 A1 *  1/2002 ............... G01N 1/22

OTHER PUBLICATIONS

International Search Report of PCT Patent Application No. PCT/CN2016/095878 dated May 24, 2017.

*Primary Examiner* — Andrey Shostak

(57) ABSTRACT

A device for collecting exhalation gas and aiding measurement of a trace component in the exhalation gas and the usage method thereof are disclosed. The device comprises an alveolar air bag for storing alveolar air collected from the breath of a subject, a cavity channel air bag for storing cavity channel air from the subject, a three-way pipe, and a mouthpiece. The three-way pipe comprises a first branch pipe, second branch pipe, and third branch pipe communicating with each other. The first branch pipe and the second branch pipe respectively extend in opposing directions along the same axis. The third branch pipe extends along a radial direction of the first branch pipe and the second branch pipe. The mouthpiece communicates with the first branch pipe. An air hole of the cavity channel air bag communicates with the second branch pipe.

4 Claims, 1 Drawing Sheet

(51) Int. Cl.
*A61B 5/097* (2006.01)
*G01N 1/22* (2006.01)

(56) References Cited

U.S. PATENT DOCUMENTS

2007/0163591 A1* 7/2007 Ross ............... A62B 19/00
128/205.12
2017/0045495 A1* 2/2017 Trowell ............. A61B 5/082

* cited by examiner

DEVICE FOR COLLECTING BREATH AND AIDING MEASUREMENT OF TRACE COMPONENT IN BREATH AND USAGE METHOD THEREOF

TECHNICAL FIELD

The present disclosure relates generally to medical device technology fields, and more particularly, to a device for collecting exhalation gas and aiding measurement of trace component in exhalation gas and a usage method thereof.

BACKGROUND

The human exhalation gas contains up to 3,000 kinds of gases, so it is necessary to eliminate the influence of non-target gases. The existing gas sampling bags only have the function of storing the gases for a short time, a further processing should be performed to remove interference when testing the various indicators of the stored gases on the machine. However, concentrating all the pre-processing steps into the testing equipment will undoubtedly increase the load on the testing equipment and prolong the time required for testing.

SUMMARY

The object of the present application is to provide a device for collecting exhalation gas and aiding measurement of trace component in exhalation gas and a usage method thereof for avoiding the problem that the existing gas sampling bags only have the function of storing the gases for a short time, but cannot eliminate the influence of non-target gases.

In a first aspect, a device for collecting exhalation gas and aiding measurement of trace component in exhalation gas is provided, comprising: an alveolar gasbag for loading alveolar gas in the exhalation gas of a collected subject, a cavity channel gasbag for loading cavity channel gas of the collected subject, a three-way catheter, and a mouthpiece; wherein the three-way catheter comprises a first branch pipe, a second branch pipe and a third branch pipe communicating with each other, wherein the first branch pipe and the second branch pipe respectively extend in opposing directions along a same axis, while the third branch pipe extends along a radial direction of the first branch pipe and the second branch pipe; wherein the mouthpiece communicates with the first branch pipe, an gas hole of the cavity channel gasbag communicates with the second branch pipe while an gas hole of the alveolar gasbag communicates with the third branch pipe; wherein an inner diameter of the second branch pipe is larger than an inner diameter of the third branch pipe.

In the device for collecting exhalation gas and aiding measurement of trace component in exhalation gas according to the present application, the inner diameter of the second branch pipe and the inner diameter of the third branch pipe have a ratio ≥1.1.

In the device for collecting exhalation gas and aiding measurement of trace component in exhalation gas according to the present application, the inner diameter of the second branch pipe and the inner diameter of the third branch pipe have a ratio range from 1.1~3.

In the device for collecting exhalation gas and aiding measurement of trace component in exhalation gas according to the present application, the inner diameter of the second branch pipe and the inner diameter of the first branch pipe are the same.

In the device for collecting exhalation gas and aiding measurement of trace component in exhalation gas according to the present application, the gas hole of the alveolar gasbag is provided with a non-return valve opening towards an inner part of the alveolar gasbag.

The device for collecting exhalation gas and aiding measurement of trace component in exhalation gas according to the present application, further comprises a background gasbag for loading an ambient gas in which the collected subject is located, and at least one reversing gasbag for removing interference components of a measured gas in collected alveolar gas and ambient gas; wherein the background gasbag is a closed or opened gasbag.

In the device for collecting exhalation gas and aiding measurement of trace component in exhalation gas according to the present application, the reversing gasbag is provided with a decontaminating element for removing the interference components of the measured gas; wherein the decontaminating element comprises at least two of a dehumidifying element containing a dehumidifying agent, a carbon dioxide removing element containing a carbon dioxide absorbent, a carbon monoxide removing element containing a carbon monoxide absorbent, a hydrogen sulfide removing element containing a hydrogen sulfide absorbent, a nitric oxide removing element containing a nitric oxide absorbent, a nitrogen dioxide removing element containing a nitrogen dioxide absorbent, an ammonia removing element containing an ammonia absorbent, a sulfur dioxide removing element containing a sulfur dioxide absorbent, and an oxygen removing element containing an oxygen absorbent.

A usage method of the above device for collecting exhalation gas and aiding measurement of trace component in exhalation gas is further provided, which comprising following steps:

S1. connecting the mouthpiece, the alveolar gasbag and the cavity channel gasbag through the three-way catheter;

S2. holding the device and putting the mouthpiece close to the collected subject's chest, and then taking a deep breath and holding the breath for 0~30 seconds;

S3. blowing through the mouthpiece to exhale as all gas in the body cavity as possible;

S4. if the alveolar gasbag is not filled up by one breath, squeezing the cavity channel gasbag to empty the gas in the cavity channel gasbag, and repeating step S2 and S3 until the alveolar gasbag is filled up.

In the usage method of the above device according to the present application, in step S4, the alveolar gasbag is not filled up means that when the alveolar gasbag is pressed by hand, the alveolar gasbag is recessed by more than 1 cm.

In the usage method of the above device according to the present application, the above device comprises a background gasbag for loading an ambient gas in which the collected subject is located, and at least one reversing gasbag for removing interference components of a measured gas in collected alveolar gas and ambient gas; wherein the background gasbag is a closed or opened gasbag; wherein if the background gasbag is closed, the ambient gas is collected by a hand pump or an electric air pump to inflate the background gasbag until the background gasbag is filled with the ambient gas in which the collected subject is located, then a cover of the background gasbag is closed, and the ambient gas is collected; if the background gasbag is opened, it is just used as a section of a background gas passage, and the ambient gas is collected directly during a detection process of the trace component.

When implementing the device for collecting exhalation gas and aiding measurement of trace component in exhalation gas and usage method thereof, following beneficial effects can be obtained. The device for collecting exhalation gas and aiding measurement of trace component in exhalation gas can eliminate the interference of the cavity channel gas in the gas exhaled after the alveolar exchange of the human body, thus reducing the pressure of the pre-processing steps and the load of the testing equipment, shortening the time required for the detection, and making the measurement results of the trace gas in the exhalation gas more accurate and reliable.

DETAILED DESCRIPTION OF THE PREFERRED EMBODIMENT

The device for collecting exhalation gas and aiding measurement of trace component in exhalation gas and usage method thereof of the present application are further illustrated with reference to the accompanying drawings and embodiments.

In the description of the present application, it is to be understood that the terms such as "center", "longitudinal", "transverse", "upper", "lower", "front", "back", "left", "right", "vertical", "horizontal", "top", "bottom", "inner", "outer", "clockwise", "anticlockwise" just refer to the orientation shown in the figures, and are merely for the purpose of facilitating the description of the present application and the simplification of the description, rather than intended to imply that the device or the component should be in a particular orientation, or should be constructed or operated in a particular orientation, so should not be understood as the limitation of the present application.

Figure 1:
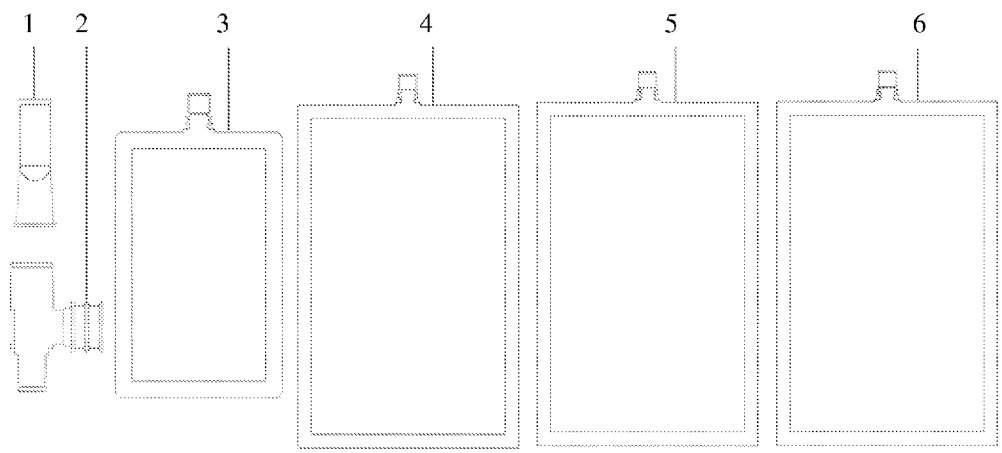
FIG. 1 is a schematic exploded view of the device for collecting exhalation gas and aiding measurement of trace component in exhalation gas according to the present application.
Figure 2:
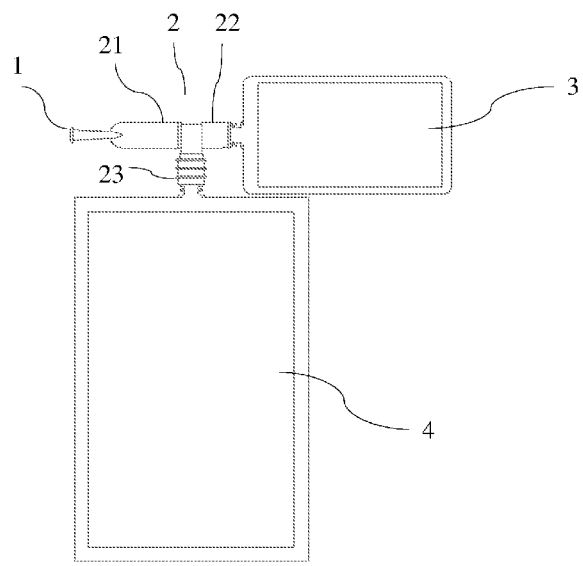
FIG. 2 is a structure assembly diagram of the mouthpiece, the alveolar gasbag and the cavity channel gasbag in the device for collecting exhalation gas and aiding measurement of trace component in exhalation gas according to the present application.

As shown in FIGS. 1-2, the device for collecting exhalation gas and aiding measurement of trace component in exhalation gas, comprises: an alveolar gasbag 4 for loading alveolar gas in the exhalation gas of a collected subject, a cavity channel gasbag 3 for loading cavity channel gas of the collected subject, a three-way catheter 2, and a mouthpiece 1. The three-way catheter 2 comprises a first branch pipe 21, a second branch pipe 22 and a third branch pipe 23 communicating with each other. The first branch pipe 21 and the second branch pipe 22 respectively extend in opposing directions along a same axis, while the third branch pipe 23 extends along a radial direction of the first branch pipe 21 and the second branch pipe 22. The mouthpiece 1 communicates with the first branch pipe 21, an gas hole of the cavity channel gasbag 3 communicates with the second branch pipe 22 while an gas hole of the alveolar gasbag 4 communicates with the third branch pipe 23. The inner diameter of the second branch pipe 22 is larger than the inner diameter of the third branch pipe 23 at the connection point of the alveolar gasbag 4. In additional, the cavity channel gasbag 3 is parallel to the direction of the exhaled gas, so the exhaled gas will enter the cavity channel gasbag 3 more preferentially, and the exhalation gas will enter the alveolar gasbag 4 after the cavity channel gasbag 3 is full, in such a way, it can be further guaranteed that the gas collected by the alveolar gasbag 4 is completely alveolar gas, thus effectively and accurately eliminating the interference of the channel gas to the measurement.

Preferably, the inner diameter of the second branch pipe 22 and the inner diameter of the first branch pipe 21 are the same. In additional, the inner diameter of the second branch pipe 22 and the inner diameter of the third branch pipe 23 preferably have a ratio $\geq 1.1$. More preferably, the inner diameter of the second branch pipe 22 and the inner diameter of the third branch pipe 23 have a ratio range from 1.1~3.

The gas hole of the alveolar gasbag 4 is provided with a non-return valve (unshown) opening towards an inner part of the alveolar gasbag 4. However, no non-return valve is provided at the gas hole of the cavity channel gasbag 3. In such a way, it can be further guaranteed that the gas collected by the alveolar gasbag 4 is completely alveolar gas, thus effectively and accurately eliminating the interference of the channel gas to the measurement.

The device for collecting exhalation gas and aiding measurement of trace component in exhalation gas according to the present application, further comprises a background gasbag 5 for loading an ambient gas in which the collected subject is located, and at least one reversing gasbag 6 for removing interference components of a measured gas in collected alveolar gas and ambient gas. The background gasbag 5 is a closed or opened gasbag. There can be one, two or more reversing gasbags 6. Preferably, there are two reversing gasbags 6 in which provided with a decontaminating element for removing the interference components of the measured gas. The decontaminating element comprises at least two of a dehumidifying element containing a dehumidifying agent, a carbon dioxide removing element containing a carbon dioxide absorbent, a carbon monoxide removing element containing a carbon monoxide absorbent, a hydrogen sulfide removing element containing a hydrogen sulfide absorbent, a nitric oxide removing element containing a nitric oxide absorbent, a nitrogen dioxide removing element containing a nitrogen dioxide absorbent, an ammonia removing element containing an ammonia absorbent, a sulfur dioxide removing element containing a sulfur dioxide absorbent, and an oxygen removing element containing an oxygen absorbent. In other embodiments, there can be a plurality of reversing gasbags 6 and in each reversing gasbag 6, the decontaminating element for removing one kind of gas is provided. For example, there can be four reversing gasbags 6, which are respectively arranged as a first reversing gasbag 6 having a dehumidifying element containing a dehumidifying agent, a second reversing gasbag having a carbon dioxide removing element containing a carbon dioxide absorbent, a third reversing gasbag having a carbon monoxide removing element containing a carbon monoxide absorbent, and a fourth reversing gasbag having sulfur dioxide removing element containing a sulfur dioxide absorbent.

The usage method of the above device for collecting exhalation gas and aiding measurement of trace component in exhalation gas is further provided, which comprising following steps:

S1. connecting the mouthpiece 1, the alveolar gasbag 4 and the cavity channel gasbag 3 through the three-way catheter 2;

S2. holding the device and putting the mouthpiece 1 close to the collected subject's chest, and then taking a deep breath and holding the breath for 0~30 seconds; preferably for 10 seconds, while in other embodiments, for 0 second, 5 seconds, 15 seconds or 30 seconds;

S3. blowing through the mouthpiece 1 to exhale as all gas in the body cavity as possible;

S4. if the alveolar gasbag 4 is not filled up by one breath, squeezing the cavity channel gasbag 3 to empty the gas in the cavity channel gasbag 3, and repeating step S2 and S3 until the alveolar gasbag 4 is filled up; in which the alveolar gasbag 4 is not filled up means that when the alveolar gasbag 4 is pressed by hand, the alveolar gasbag 4 is recessed by more than 1 cm;

S5. when the alveolar gasbag 4 is filled up, it is pulled off and closed by a cover, and then the alveolar gas collection is finished.

In addition, the gas is collected after getting up in the morning and before 12 o'clock. Subject requirements: On an empty stomach, the subject should not smoke within 24 hours before gas collection. The alveolar gas sample must be measured within 5 days.

If the background gasbag 5 is closed, the ambient gas is collected by a hand pump or an electric air pump to inflate the background gasbag 5 until the background gasbag 5 is filled with the ambient gas in which the collected subject is located, then a cover of the background gasbag 5 is closed, and the ambient gas is collected. If the background gasbag 5 is opened, it is just used as a section of a background gas passage, and the ambient gas is collected directly during a detection process of the trace component.

It is to be understood that those skilled in the art can make modifications and changes in the form of the above description, and all modifications and variations are intended to be included within the scope of the appended claims.

What is claimed is:

1. A usage method of a device for collecting exhalation gas and aiding measurement of trace components in exhalation gas, wherein the device for collecting exhalation gas and aiding measurement of trace components in exhalation gas comprises an alveolar gasbag (4) for loading alveolar gas in the exhalation gas of a collection subject, a cavity channel gasbag (3) for loading cavity channel gas of the collection subject, a tee fitting (2), and a mouthpiece (1); wherein the tee fitting (2) comprises a first branch pipe (21), a second branch pipe (22) and a third branch pipe (23) communicating with each other, wherein the first branch pipe (21) and the second branch pipe (22) respectively extend in opposing directions along a same axis, while the third branch pipe (23) extends along a radial direction of the first branch pipe (21) and the second branch pipe (22); wherein the mouthpiece (1) communicates with the first branch pipe (21), a gas hole of the cavity channel gasbag (3) communicates with the second branch pipe (22) while a gas hole of the alveolar gasbag (4) communicates with the third branch pipe (23); wherein an inner diameter of the second branch pipe (22) is larger than an inner diameter of the third branch pipe (23); and wherein the device for collecting exhalation gas and aiding measurement of trace components in exhalation gas further comprises a background gasbag (5) for loading an ambient gas in which the collection subject is located, and four reversing gasbags (6) for removing interference components of a measured gas in collected alveolar gas and ambient gas, wherein each of the reversing gasbags (6) is provided with a respective decontaminating element;

wherein the usage method comprises the following steps:

S1. connecting the mouthpiece (1), the alveolar gasbag (4) and the cavity channel gasbag (3) through the tee fitting (2);

S2. holding the device and putting the mouthpiece (1) close to the collection subject's chest, and then taking a deep breath and holding the breath for 0-30 seconds;

S3. blowing through the mouthpiece (1) to exhale as much gas as possible;

S4. if the alveolar gasbag (4) is not filled up by one breath, squeezing the cavity channel gasbag (3) to empty the gas in the cavity channel gasbag (3), and repeating step S2 and S3 until the alveolar gasbag (4) is filled up;

S5. removing the interference components of the measured gas by the four reversing gasbags (6), wherein the four reversing gasbags comprise a first reversing gasbag having as its decontaminating element a dehumidifying element containing a dehumidifying agent, a second reversing gasbag having as its decontaminating element a carbon dioxide removing element containing a carbon dioxide absorbent, a third reversing gasbag having as its decontaminating element a carbon monoxide removing element containing a carbon monoxide absorbent, and a fourth reversing gasbag having as its decontaminating element a sulfur dioxide removing element containing a sulfur dioxide absorbent; and S6. collecting ambient gas by the background gasbag (5), wherein: if the background gasbag (5) is closed, the ambient gas is collected by a hand pump or an electric air pump to inflate the background gasbag (5) until the background gasbag (5) is filled with the ambient gas in which the collection subject is located, then a cover of the background gasbag (5) is closed, and the ambient gas is collected; and if the background gasbag (5) is opened, it is used as a section of a background gas passage, and the ambient gas is collected directly during a detection process of the trace components;

wherein the inner diameter of the second branch pipe (22) is larger than the inner diameter of the third branch pipe (23) at a connection point of the alveolar gasbag (4) and the cavity channel gasbag (3) is parallel to a direction of an exhaled gas, so the exhaled gas will enter the cavity channel gasbag (3) more preferentially, and the exhalation gas will enter the alveolar gasbag (4) after the cavity channel gasbag (3) is full; and wherein the inner diameter of the second branch pipe (22) and the inner diameter of the third branch pipe (23) have a ratio range from 1.1-3.

2. The usage method according to claim 1, wherein in step S4, the alveolar gasbag (4) is not filled up when if the alveolar gasbag (4) is pressed by hand, the alveolar gasbag (4) is recessed by more than 1 cm.

3. The usage method according to claim 1, wherein an inner diameter of the second branch pipe (22) and an inner diameter of the first branch pipe (21) are the same.

4. The usage method according to claim 1, wherein the gas hole of the alveolar gasbag (4) is provided with a non-return valve opening towards an inner part of the alveolar gasbag (4).

* * * * *